United States Patent [19]

Armond et al.

[11] Patent Number: 4,677,246

[45] Date of Patent: Jun. 30, 1987

[54] PROTOGYNY IN *ZEA MAYS*

[75] Inventors: Paul A. Armond, Ledyard; Peter M. Orr, Pawcatuck, both of Conn.

[73] Assignee: Dekalb-Pfizer Genetics, DeKalb, Ill.

[21] Appl. No.: 727,503

[22] Filed: Apr. 26, 1985

[51] Int. Cl.$^4$ .............................................. A01H 1/02
[52] U.S. Cl. ......................................... 800/1; 47/58; 47/DIG. 1
[58] Field of Search .................. 47/58, DIG. 1; 800/1

[56] References Cited

PUBLICATIONS

Iltis et al., Science, vol. 203, Jan. 12, 1979, pp. 186–188.
Magaja and Pischedda, *Maize Genetics Cooperation, News Letter*, vol. 58, pp. 130–132, Apr. 30, 1984.
Nault and Findley, *Ohio Report*, Nov.–Dec. 1981, pp. 90–92.
Camara-Hernandez and Mangelsdorf, *Maize Genetics Cooperation, News Letter*, vol. 55, pp. 15–17, 1981.
Mangelsdorf et al., *Maize Genetics Cooperation, News Letter*, vol. 55, pp. 19–21, 1981.

*Primary Examiner*—Robert E. Bagwill
*Attorney, Agent, or Firm*—Charles J. Knuth; Peter C. Richardson; Robert F. Sheyka

[57] ABSTRACT

Novel protogynous *Zea mays* plants are disclosed, including a novel protogynous inbred line, LALGI. Also disclosed are a process to produce such *Zea mays* plants and hybrids resulting from crossing such plants with other inbred lines such as Iowa Stiff Stalk Synthetic Lines.

12 Claims, No Drawings

PROTOGYNY IN ZEA MAYS

BACKGROUND OF THE INVENTION

Zea mays, the modern maize or corn of commerce, is normally a protandrous species, that is the male flowering parts (anthers) dehisce before the female parts (silks) extrude. This system probably evolved in response to the selective advantage gained by cross-pollination and, under ordinary conditions, it works well. However, under stress conditions in the field, an exagerated silk delay occurs resulting in a low fertilization rate and low yield because most of the pollen has been shed and blown away before the receptive female parts appear. Stress induced silk delay is a primary cause of reduced yield in Zea mays.

Zea diploperennis, a wild relative of modern maize, is protogynous, silking well before the pollen is produced. This protogynous habit is preserved even under stress conditions. Zea diploperennis was described as a new species by Iltis et al. Science, vol. 203, Jan. 12, 1979, P. 186–188. The protogynous nature of the species and its crosses was first noted by Magoja and Pischedda in *Maize Genetics Cooperation News Letter* 58, P. 130–132 Department of Agronomy and U.S. Department of Agriculture, University of Missouri, Columbia, Mo., April 30, 1984.

Zea mays and Zea diploperennis have been crossed previously to achieve certain characteristics in the offspring. Nault and Findley (*Ohio Report*, Nov.-Dec., 1981, P. 90-92) crossed these two species to induce resistance to certain viral and mycoplasmal diseases in corn. Camara-Hernandez (*Maize Genetics Cooperation News Letter* 55, P. 15-17, 1981 and Mangelsdorf et al. (*Maize Genetics Cooperation News Letter* 55, P. 19-21, 1981) made the same cross with the goal of developing a perennial corn plant.

The present invention for the first time solves the problem of the serious economic loss brought about by poor maize yield when fields are stressed and silking is delayed. The solution involves the introduction of the genes for protogyny from Zea diploperennis into Zea mays.

SUMMARY OF THE INVENTION

The present invention comprises a method to induce protogyny in plants of Zea mays comprising introducing into Zea mays genes for the trait from plants of Zea diploperennis and subsequently selecting for the trait. The method wherein the introduction is by means of crossing plants of the two species is preferred. Also preferred is the method wherein the $F_1$ generation plants so produced are backcrossed with Zea mays.

In the method of this invention Zea mays can be employed advantageously as the female parent and also as the male parent in the cross. The method is preferred wherein the Zea mays is inbred line LH38.

A further feature of this invention is protogynous Zea mays produced according to the method above, especially Zea mays designated as inbred line LALG1. A further feature of this invention is protogynous Zea mays.

A final feature of this invention is hybrid Zea mays plants produced by crossing protogynous Zea mays plants produced by the method above and other inbred lines such as an Iowa Stiff Stalk Synthetic line of Zea mays, especially those plants in which the protogynous parent is inbred line LALG1, and most especially those wherein the Iowa Stiff Stalk Synthetic line is inbred line A632Ht and the protogynous parent is inbred line LALG1.

DETAILED DESCRIPTION OF THE INVENTION

In the initial phase of experimental work that led to this invention Zea diploperennis was crossed with Zea mays, using Zea mays as the female parent in the cross. Kernels developed only at the distal end of the ears, probably as a result of the short length of the Zea diploperennis pollen tubes. In subsequent crosses Zea mays has been used as the male parent and the present invention encompasses both possibilities. In the initial cross, inbred line LH38 of Zea mays was used. This line is publically available from Holden's Foundation Seeds, Williamsburg, Iowa. The choice of the Zea mays line to be used as a parent will be at the discretion of the plant breeder, any variety being possible, but generally an elite inbred line will be selected which has desirable characteristics for the final product to be produced. Seeds of Zea diploperennis are publically available from Hugh H. Iltis, Univ. of Wisconsin, Madison, Wis. and W.C. Galihat, Univ. of Massachusetts, Amherst, Mass.

The hybrid seed from the initial cross was harvested and planted and the plants were grown to sexual maturity. All $F_1$ hybrid plants exhibited precocious silking ranging from 9 to 14 days. Some of the $F_1$ hybrid plants were drought stressed by mid/late vegetative phase water deprivation and these plants also silked prior to pollen shedding.

All kernels formed on the $F_1$ hybrid plants developed abnormally large endosperms which swelled beyound the confines of the glumes. Morphologically, the plants appeared tall and multi-branched. Selection for the protogynous trait was made on the $F_1$ generation plants by noting dates of silk extrusion and anther dehiscence. Those plants selected were entered into a backcross program using LH38 as the recurrent parent. The progeny of this backcross ($BC_1$) generation was planted in a greenhouse and grown to reproductive development stage. The precocity of silking in these plants was up to 5 days.

A second backcross was made using LH38 as the male parent or pollen donor. The seeds resulting from this backcross ($BC_2$) were planted and the resulting plants were of single stalk habit with large tassels and with the general appearance of LH38. Plant stature was quite variable. Again the precocity of silking was about 4 days. Another backcross was made again using LH38 pollen and hybrids selected as described above as the female parent. In this $BC_3$ generation, the plants were similar in appearance to the $BC_2$ plants and the precocity of silking was 3–4 days.

A fourth and fifth backcross were also made with the LH38 as male parent. The plants resulting from these backcrosses again resembled LH38 and exhibited precocious silking of 4–5 days. It is interesting to note that LH38 plants grown under identical conditions to these backcrosses showed a silking delay of about 3 days. The Table below shows the results of field observations on these backcross generations.

TABLE

Analysis of Silking Capability in Backcross Generations of LH38 x Z. diploperennis

| Backcross Generation | Precocious Silking* | Synchronous* | Silk Delayed* | Percent Precocious Silking | Percent Synchronous and Precocious |
| --- | --- | --- | --- | --- | --- |
| BC1 | 108 | 63 | 49 | 49.1 | 77.7 |
| BC2 | 541 | 459 | 360 | 39.8 | 73.5 |
| BC3 | 333 | 315 | 396 | 31.9 | 62.1 |
| BC4 | 135 | 235 | 660 | 13.1 | 35.9 |
| BC5 | 321 | 581 | 1034 | 16.7 | 46.6 |
| LH38 (control) | 31 | 132 | 415 | 5.4 | 28.2 |

*numbers of plants

The fifth backcross generation was planted in the greenhouse and protogynous plants identified. Some selections from this population were selfed. The $BC_5S_1$ material was field planted in Hawaii and the protogynous plants selfed. The seed from these selections ($BC_5S_2$) were again field planted in Hawaii. The $BC_5S_3$ seed from a selected plant from this population was given the designation LALGI, based on its protogynous habit and its overall desirable agronomic phenotype. Seeds of LALGI have been deposited with In Vitro International, Inc., 7885 Jackson Road, Suite 4, Ann Arbor, Mi. 48103, under accession number IVI-10055.

The line designated as LALGI was crossed with inbred line A632Ht to produce a corn hybrid expected to have significant commercial advantage.

We claim:

1. A method to induce protogyny in plants of *Zea mays* comprising introducing into *Zea mays* genes for said trait from plants of *Zea diploperennis* and subsequently selecting for said trait.
2. The method of claim 1 wherein said introduction is by means of crossing plants of said species.
3. The method of claim 2 wherein the $F_1$ generation plants produced are backcrossed with *Zea mays*.
4. The method of claim 2 wherein *Zea mays* is employed as the female parent in said cross.
5. The method of claim 2 wherein *Zea mays* is employed as the male parent in said cross.
6. The method of claim 1 wherein said *Zea mays* is inbred line LH38.
7. *Zea mays* produced according to claim 1.
8. *Zea mays* produced according to claim 1 and designated as inbred line LALGl.
9. Protogynous *Zea mays*.
10. Hybrid *Zea mays* plants produced by crossing protogynous *Zea mays* plants produced by the method of claim 1 other inbred lines such as an Iowa Stiff Stalk Synthetic line of *Zea mays*.
11. Hybrid *Zea mays* plants produced according to claim 10 wherein said protogynous plants are inbred line LALGl.
12. Hybrid *Zea mays* plants produced according to claim 10 wherein said Iowa Stiff Stalk Synthetic line is inbred A632Ht.

* * * * *

UNITED STATES PATENT AND TRADEMARK OFFICE
CERTIFICATE OF CORRECTION

PATENT NO. : 4,677,246

DATED : June 30, 1987

INVENTOR(S) : Paul A. Armond & Peter M. Orr

It is certified that error appears in the above-identified patent and that said Letters Patent is hereby corrected as shown below:

Title page:

In the abstract, "LALGI" should be ---LALG1---

At Column 2, line 26 "Galihat" should be ---Galinat---

At Column 2, line 26 "beyound" should be ---beyond---

At Column 3, line 23, "LALGI" should be ---LALG1---

At Column 3, line 25, "LALGI" should be ---LALG1---

At Column 3, line 28, "LALGI" should be ---LALG1---

Signed and Sealed this

Twenty-ninth Day of December, 1987

Attest:

DONALD J. QUIGG

Attesting Officer

Commissioner of Patents and Trademarks